United States Patent [19]

Randolph

[11] 4,183,729
[45] Jan. 15, 1980

[54] APPARATUS AND METHOD FOR DETERMINING CRYSTALLIZATION PROPERTIES OF URINE

[75] Inventor: Alan D. Randolph, Tucson, Ariz.

[73] Assignee: University Patents, Inc., Norwalk, Conn.

[21] Appl. No.: 925,172

[22] Filed: Jul. 17, 1978

Related U.S. Application Data

[63] Continuation of Ser. No. 881,655, Feb. 27, 1978, abandoned.

[51] Int. Cl.$^2$ .................... G01N 15/06; G01N 21/22; G01N 33/16
[52] U.S. Cl. ................................. 23/230 B; 422/68; 422/245
[58] Field of Search .................. 23/230 B; 422/245, 68

[56] References Cited
PUBLICATIONS

Chemical Abstracts, 69:70908(a) (1968).
Chemical Abstracts, 81:83050n (1974).
Chemical Abstracts, 82:29413r (1975).

*Primary Examiner*—Sidney Marantz
*Attorney, Agent, or Firm*—Martin Novack

[57] ABSTRACT

An apparatus and method for determining crystallization properties of urine to study stone formation therein. A continuous crystallizer is loaded with a fluid, or mother liquor, containing synthetic urine and an aliquot of natural urine. The mother liquor is recirculated from an output of the continuous crystallizer back to an input thereof. After stabilization has been achieved in the crystallizer, the crystal populations of the fluid are measured. Measurement is performed by sampling the contents of the continuous crystallizer and measuring the crystal populations of the sample. In the preferred embodiment of the method, calcium and oxalate ions are added to the fluid to study the formation of calcium oxalate in urine. The recirculating fluid is saturated with calcium and oxalate ions using a saturator loaded with calcium oxalate crystals. To study precipitation of crystals, or the absence thereof, in the circulating mother liquor, calcium and oxalate ions are also fed, from separate sources, to the continuous crystallizer. In the apparatus of the invention, a recirculating loop from and to the continuous crystallizer includes a surge tank, a pump, a packed bed saturator, and suitable filters. Sampling is performed using a continuous flow sampling cell, and a particle counter generates an output which is a measure of the crystal populations of the continuous crystallizer. A computing module can then be employed to calculate crystallization properties of the mother liquor as a function of the crystal populations.

32 Claims, 1 Drawing Figure

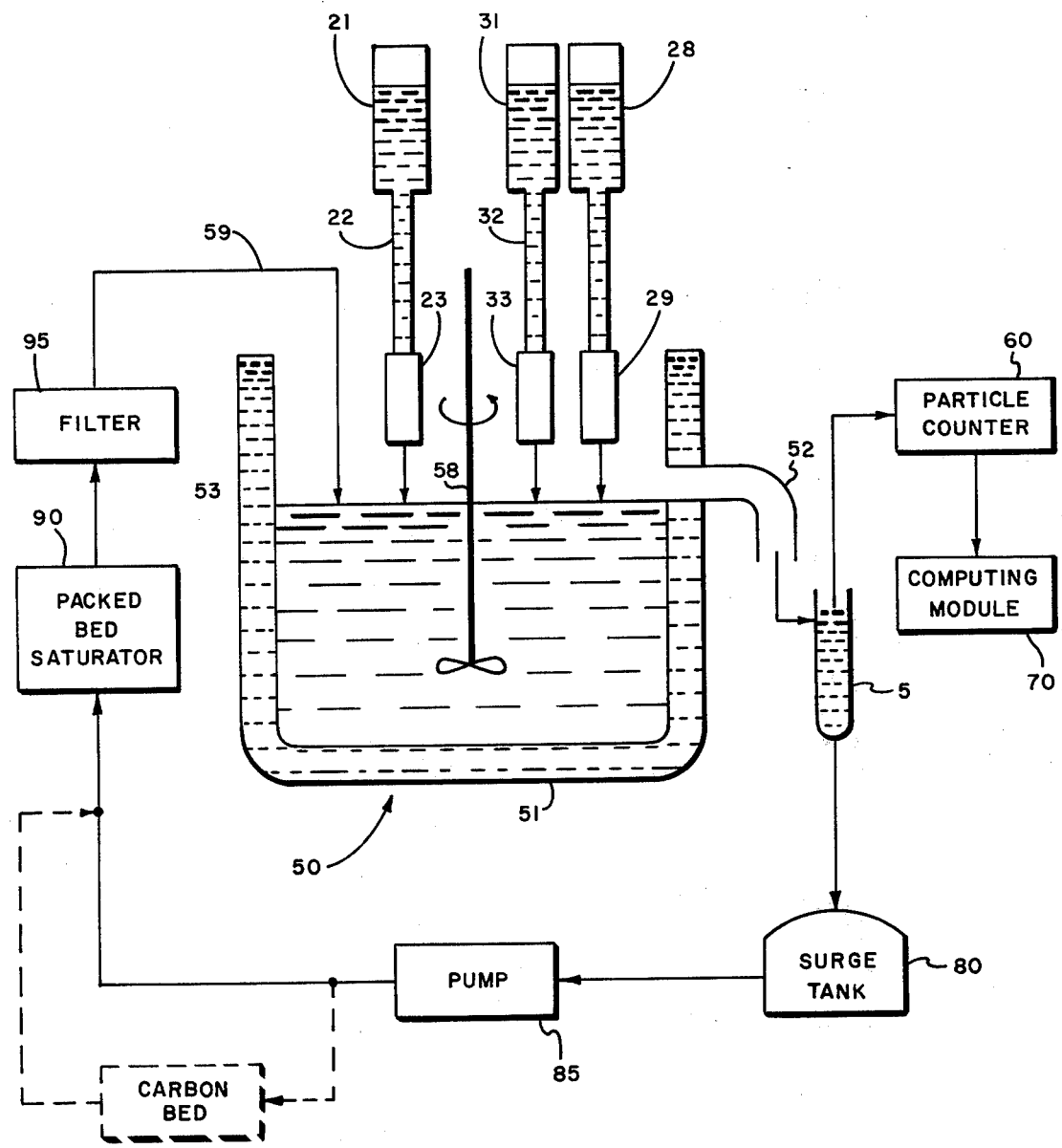

APPARATUS AND METHOD FOR DETERMINING CRYSTALLIZATION PROPERTIES OF URINE

This is a continuation, of application Ser. No. 881,655, filed Feb. 27, 1978, abandoned.

BACKGROUND OF THE INVENTION

This invention relates to techniques for analyzing body fluids and, more particularly, to a method and apparatus for determining crystallization properties of urine.

The mechanisms of renal stone formation are not fully understood. This is particularly true of calcium oxalate and calcium phosphate stones which are quite common. Some investigators have offered evidence in support of the theory that the dominating cause of calcium oxalate stone formation is supersaturation of urine with calcium ions and oxalate ions. These investigators have generally set forth ex-vivo evidence in support of this "supersaturation" theory, but the causes of chemical changes which lead to the stone formation are not fully explained. It would appear that if supersaturation of urine alone causes renal calculi, correction of this cause by limitation of ion excretion might be readily achievable. However, treatment to reduce supersaturation of crystallizable ions has not been found completely successful in arresting stone disease.

Other investigators have found evidence to support the theory that normal urine contains substances that inhibit the nucleation and/or growth of, or effect the solubility of, calcium oxalate. There have been certain indications, again not fully explained, that certain inhibiting substances found in normal urine are absent from the urine of stone formers.

It has been demonstrated that the particle size distribution of calcium oxalate crystals in fresh urine from recurrent stone formers is quite different than the distribution found in "control" non-stone-formers under the same conditions of dietary and fluid intake. For example, in an article entitled "Calcium Oxalate Crystalluria and Inhibitors of Crystallization in Recurrent Renal Stone-formers," which appeared in Volume 43 of "Clinical Science," it was reported that the crystals excreted by the controls were small and belong to a unimodal distribution, whereas those excreted by the stone-formers belong to a distribution which contained a second peak of much larger particles. In the same article, it was suggested that the urines of the controls contained an inhibitor of the growth and aggregation of calcium oxalate crystals in vitro and that the inhibitor was deficient in the urines of the recurrent stone-formers. While these findings are useful, it is necessary to enhance available data with information regarding the mechanisms of crystal growth and to measure the effects of the chemicals thought to be effective inhibitors, such as to determine the effectiveness of various treatments in producing the desired inhibiting action.

In an article entitled "The Inhibitory Effect of Urine on Calcium Oxalate Precipitation," which appeared in Volume 12, No. 6 of "Investigative Urology," there was destribed experiments in which a solution of natural urine in a buffered mixture containing calcium ions and oxalate ions had a measurable inhibitory effect on the formation of calcium oxalate precipitate. In these experiments the precipitate was recovered using a filter and calcium content was measured using flame photometry. In an attempt to determine the extent of inhibition of precipitation caused by the natural urine due to those urinary constituents known to effect calcium oxalate solubility, an "artificial urine," consisting of a mixture of nine salts and urea, was substituted for the natural urine and the experiments were repeated. In both cases (natural as well as artificial urine), it was found that the degree of inhibition of precipitate formation was related to the concentration of the urine in the solution. The "artificial urine" was found to have some inhibitory effect, but less than that of the same amount of natural urine.

The described prior art techniques, while useful, are limited by practical problems which arise in the attempt to isolate and determine the precise nature of the crystal forming and/or inhibiting effect of constituents in highly complicated natural urine. On the one hand, it would appear desirable to utilize relatively high concentrations of natural urine in performing experiments, since this apparently amplifies the effect to be measured and renders observations easier. On the other hand, due to the complex, variable, and still somewhat unknown nature of the constituents of natural urine and the reactions which occur in natural urine, the experimenter using relatively higher concentrations thereof must be concerned with "background reactions" which may tend to disturb measurements being taken by introducing unknown factors. A further practical limiting factor is that the amount of fresh natural urine from a particular subject being studied is limited by the subject's output, typically less than 2,000 milliliters per day under normal fluid intake conditions. Thus, techniques which require relatively large volumes of urine or numerous experiments to be performed using the urine of a given subject (each requiring a volume of urine) are rendered impractical.

In an article entitled "The Concept of a Continuous Crystallizer—Its Theory and Application to In Vivo and In Vitro Urinary Tract Models," by B. Finlayson, which appeared in Volume 9, No. 4 of "Investigative Urology," there is described an attempt at employing a "continuous crystallizer" for experiments wherein feed solutions including urine plus calcium and oxalate ions were crystallized under steady state conditions to determine properties of the crystallization process. The article cites a series of prior publications by Randolph et al which disclose various chemical engineering applications of particle balance to continuous crystallizers. In the Finlayson article, a "continuous crystallizer" is defined as any chamber continuously receiving a stream of supersaturated liquid and continuously ejecting a stream of liquid plus suspended particles. Finlayson reported employing a 550 milliliter continuous crystallizer into which were dripped the urine plus the salts including calcium and oxalate ions. After a number of system cycles had elapsed (i.e., cycles of mixing and removing to achieve a "steady state" of crystallization), measurements were taken on the reaction chamber contents by filtering to obtain the crystals and then making photomicrographs.

In the U.S. Pat. No. 4,025,307, there is disclosed a method and apparatus for determining crystallization properties, such as the particle kinetics, of urine, which overcame a number of the existing prior art problems. In the patent, feed solutions containing synthetic urine and an aliquot of natural urine are combined in a continuous crystallizer, and the particle densities or crystal populations of the contents of the crystallizer are measured. The particle kinetics, such as nucleation and growth rate of the crystals, can then be calculated as a function of the measured particle densities. In one form of the apparatus disclosed in the referenced patent, the volume of the continuous crystallizer is of the order of 100 milliliters, it having been found that this unusually small volume does not interfere with the obtainment of proper steady state continuous crystallization and the relatively accurate measurement of crystallization kinetics. Using the techniques disclosed in the referenced patent, the synthetic urine contributes necessary stability and control so that crystallization properties can be measured without undue "background" reactions, yet enough natural urine is present to yield sufficient quantities of the constituents being measured to provide adequate sensitivity. The two feed solutions, respectively contain calcium and oxalate ions in amounts sufficient to cause supersaturation in the continuous crystallizer and contain components of the type necessary to obtain weddelite-type crystals of calcium oxalate in the dihydrate form (this being the type of calcium oxalate crystals generally formed in human urine). Only relatively small amounts of natural urine are needed, and the relatively small size of the continuous crystallizer is advantageous in reducing the total amount of reagents (from the feeds) necessary to perform a given test.

While the advantages of the techniques disclosed in the U.S. Pat. No. 4,025,307 are apparent, applicant has found that various aspects thereof can stand improvement. For example, it is a property of a continuous crystallizer, such as a so-called "mixed suspension mixed product removal" crystallizer of the type preferred in the referenced patent, that reagents are continually fed to th crystallizer unit and overflow therefrom. This is done to obtain and maintain a "steady state" condition under which reactions can be studied. However, the total volume of reagents utilized in this procedure is typically many times the volume of the continuous crystallizer chamber. Accordingly, a substantial volume of reagents is required for each test, thereby compromising the practicality of the test procedure. Further, it would be advantageous to have more closely controllable and efficient means of maintaining the supersaturation level of calcium oxalate in the continuous crystallizer.

It is generally an object of the present invention to provide improvement over the technique set forth in the above-referenced U.S. Pat. No. 4,025,307.

SUMMARY OF THE INVENTION

The present invention is directed to an apparatus and method for determining crystallization properties of urine to study stone formation therein. In accordance with the method of the invention, a continuous crystallizer is loaded with a fluid, or mother liquor, containing synthetic urine and an aliquot of natural urine. The mother liquor is recirculated from an output of the continuous crystallizer back to an input thereof. After stabilization has been achieved in the crystallizer, the crystal populations of the fluid are measured. Measurement is preferably performed by sampling the contents of the continuous crystallizer and measuring the crystal populations of the sample. In the preferred embodiment of the method of the invention, calcium and oxalate ions are added to the fluid to study the formation of calcium oxalate in urine. The recirculating fluid is saturated with calcium and oxalate ions using a saturator loaded with calcium oxalate crystals. To study precipitation of crystals, or the absence thereof, in the recirculating mother liquor, calcium and oxalate ions are also fed, from separate sources, to the continuous crystallizer.

In the preferred form of the apparatus of the invention, a recirculating loop from and to the continuous crystallizer includes a surge tank, a pump, a packed bed saturator, and suitable filters. Sampling is performed using a continuous flow sampling cell, and a particle counter generates an output which is a measure of the crystal populations of the continuous crystallizer. A computing module can then be employed to calculate crystallization properties of the mother liquor as a function of the crystal populations.

Further features and advantages of the invention will become more readily apparent from the following detailed description when taken in conjunction with the accompanying drawing.

BRIEF DESCRIPTION OF THE DRAWING

The drawing is a schematic diagram, partially in block form, which illustrates an apparatus in accordance with the invention and which can be utilized to practice the method of the invention.

DESCRIPTION OF THE PREFERRED EMBODIMENT

Referring to FIG. 1, there is shown a schematic representation, partially in block form, of an apparatus in accordance with an embodiment of the invention and which is useful in performing the method in accordance with the invention. A continuous crystallizer 50 is of the continuous mixed suspension mixed product removal type and, in some functional respects, of the general type described in an article entitled, "Size Distribution Analysis in Continuous Crystallization" which appeared in "Chemical Engineering Progress Series," Volume 65, No. 95. In particular, the receptacle or chamber 51 of crystallizer 50 is continuously well stirred by a stirring rod 58 (powdered by means not shown), and the amount of mixed product in the receptacle is maintained substantially constant by an overflow drain 52 and a source 59, to be described, which provides a constant flow of solution to the chamber receptacle. The chamber 51 is preferably maintained at a constant temperature of 38° C. which simulates human body temperature, this being achieved by a constant temperature jacket 53 which continually receives recirculated fluid (by means not shown) from a constant temperature bath (not shown).

In the present invention, unlike the typical prior art continuous crystallizer, the overflow solution from the crystallizer receptacle is reused, after appropriate treatment, as a feed source (59); i.e., a substantially closed loop system flow is effected. Specifically, the overflow from drain 52 is coupled to a feed surge tank 80 which is, in turn, coupled to a fixed volume pump 85. The pump 85 is coupled to a packed bed saturator 90 which is coupled, via a filter 95, as a source 59 back into the chamber 51.

The fluid overflow of chamber 51 is sampled by a continuous flow sampling cell 5, which may typically be of the type manufactured by Particle Data Inc. A particle counter 60 is responsive to the fluid in the sampling cell and operates to generate an output which is a measure of the crystal populations of the steady state contents of chamber 51. This information is coupled to a computing module 70 which calculates the crystallization properties (i.e., particle kinetics) of the contents of the chamber 51 as a function of the crystal populations.

Operation of a computing module is described, for example, in the above-referenced U.S. Pat. No. 4,025,307. In the embodiment of FIG. 1, a pair of feed receptacles 21 and 31 are provided and contain feed solutions (to be described) which are fed, at a relatively slow rate (compared to the fed back flow from source 59) into the chamber 51 of the continuous crystallizer. The feed receptacles 21 and 31 are respectively coupled, via tube 22 and continuous feed pump 23, and via tube 32 and continuous feed pump 33, to the chamber 51. A single pump unit may, however, be shared, if desired. A receptacle 28 is provided from which natural urine may be fed to the chamber 50 via feed pump 29.

In operation, the continuous crystallizer, and its associated closed loop, is initially filled with synthetic urine. Synthetic urine as defined herein, is intended to mean any urine-like solution containing components of the type necessary to study crystallization properties in similar natural urine. Typically, and as is described in the refered U.S. Pat. No. 4,025,307, the synthetic urine comprises a plurality of salts dissolved in water to obtain the cations sodium, potassium, calcium ammonium and magnesium, and the anions chloride, sulfate, oxalate and phosphate. The synthetic urine, plug an aliquot of natural urine, comprises a mother liquor which is continuously recirculated in the system FIG. 1. The aliquot of natural urine may be contained in the feed originally used to fill the system, or may be added afterwards via the urine feed 28.

The rate of flow, as determined by pump 85, is set to maintain the overall desired retention time in the continuous crystallizer 50, for example 10 minutes in a 800 milliliter chamber. Precipitation, or the absence thereof, is studied or tested by feeding excess calcium and oxalate ion into the continuous crystallizer using feeds 21 and 31, in water, synthetic urine, or mixtures thereof, and thus can be fed to the continuous crystallizer at a relatively low rate. Particles which form are captured, to some extent, by the packed bed saturator 90, with remaining particles being removed by one or more filters 95. Filter 95 may comprise, for example, a pair of Pall filters having 5 and 0.45 micron retaining characteristics (filter characteristics). Saturation of the recirculating flow with calcium and oxalate ions is insured by loading the packed bed saturator with calcium oxalate crystals.

The described fluid system would typically be utilized for a given patient and continue to be used until tests are complete. Organ impurities can be removed in the circulating loop using, for example, the carbon bed 91 (shown in dashed line). Typically, in the case of a given patient, after one or more tests have been performed, the flow can be diverted through the carbon bed periodically to remove organic inhibitors, and a fresh sample of urine can then be injected into the mother liquor (e.g. via feed 28) with the carbon bed being removed from the loop. Alternatively, the carbon bed can be permanently retained in the loop. The relatively small amounts of fluid added to the continuous crystallizer via feeds 21 and 31 are substantially equal to the volume utilized by the sampling cell. Any difference is accounted for by the feed surge tank 80, so a steady pump rate can be employed.

CLOSED-LOOP CRYSTALLIZATION OF CALCIUM OXALATE DIHYDRATE

Procedure

1. Synthetic urine saturated to an approximately 3 to 1 molar ratio of calcium, ($Ca^{++}$), to oxalate, ($C_2O_4^{--}$), was made with the following constituents dissolved in 3 liters of ultrapure, deionized water.

| | |
|---|---|
| $Na_2SO_4$ | 9.99 gms |
| $NH_4Cl$ | 9.54 gms |
| $KCl$ | 24.93 gms |
| $MgSO_4 \cdot 7H_2O$ | 6.00 gms |
| $NaH_2PO_4 \cdot H_2O$ | 12.36 gms |
| $Na_2HPO_4$ | 1.74 gms |
| $NaCl$ | 27.75 gms |
| $Na_3C_6H_5O_7 \cdot 2H_2O$ | 2.40 gms |
| $CaCl_2$ | 0.464 gms |
| $Na_2C_2O_4$ | 0.336 gms |

2. Approximately 900 gms of $CaC_2O_4 \cdot H_2O$ was added as powder into the center of the saturation column and covered with glass beads.

3. The urine solution was pumped at 90 mls/min from the surge tank through the 600 ml saturation column into a series-parallel combination of P filters to remove all particles greater than 0.2 microns.

4. Clear, saturated urine passed through the filters into the MSMPR crystallizer. The volume of the crystallizer was held at approximately 800 mls so that the resulting retention time, $\tau$, was 8.97 minutes. The propeller was rotated at 600 rpms.

5. A 0.552 M $CaCl_2$ solution, ($CaCl_2$ in $H_2O$), was dripped into the crystlizer from above through a glass feed tube at 0.48 ml/min. A 0.276 M $Na_2C_2O_4$ solution, ($Na_2C_2O_4$ in synthetic urine), was also dripped into the crystallizer from above at 0.99 ml/min. Overall, approximately $2.70 \times 10^{-4}$ moles/min. of each entered the crystallized throughout the run.

6. The urine solution and particlates discharged from the crystallizer through the liquid-level controller and into the particle sampling tube. Here the product stream was analyzed by pulling a 2 ml sample of the product stream through the 190 micron orifice of the Particle Data Instrument. Through the appropriate string of computer command the kinetics of the product stream were computed and outputed as hard copy.

7. Solution flowed from the sampling tube back into the surge tank to repeat the cycle. A sample was analyzed every 10 minutes throughout the run until steady-state was achieved. (10 retention times)

8. A 40° C. temperature was maintained by circulating heating water from a constant temperature bath through water jackets on the saturation column and crystallizer.

The resultant average statistics for two sample counts, ea. 15 minutes apart, are as follows

| Sample Number | Summary of Steady St. | | |
|---|---|---|---|
| | G, $\mu$/min | $B^o$, no./cc-min | $M_T$, mg/l |
| 1 | 0.310 | 3,590 | 2.95 |
| 2 | 0.298 | 3,770 | 2.65 |

In the above table the variables have the following meaning

G = linear growth rate, $\mu$/min
$B^o$ = nucleation rate, no/cc-min $M_T$ = slurry density (as dehydrate), mg/l
R = dimensionless correlation coefficient.

I claim:

1. A method for determining crystallization properties of urine to study stone formation therein, comprising the steps of:
   loading a continuous crystallizer with a fluid containing synthetic urine and an aliquot of natural urine;
   recirculating the fluid from an output of said continuous crystallizer back to an input of said continuous crystallizer; and
   measuring the crystal populations of the fluid.

2. The method as defined by claim 1 wherein the step of measuring the crystal populations of the fluid includes the steps of sampling the contents of said crystallizer and measuring the crystal populations of the sample.

3. The method as defined by claim 1 further comprising the step of adding calcium and oxalate ions to said fluid.

4. The method as defined by claim 2 further comprising the step of adding calcium and oxalate ions to said fluid.

5. The method as defined by claim 4 wherein the step of adding calcium and oxalate ions comprises saturati the recirculating fluid using a calcium oxalate saturator.

6. The method as defined by claim 5 wherein the step of adding calcium and oxalate ions further comprises feeding separate sources of calcium and oxalate ions to said fluid.

7. The method as defined by claim 1 further comprising the step of filtering the recirculating mother liquor.

8. The method as defined by claim 3 further comprising the step of filtering the recirculating mother liquor.

9. The method as defined by claim 6 further comprising the step of filtering the recirculating mother liquor.

10. The method as defined by claim 1 wherein the output of said continuous crystallizer is the fluid overflow therefrom.

11. The method as defined by claim 3 wherein the output of said continuous crystallizer is the fluid overflow therefrom.

12. The method as defined by claim 9 wherein the output of said continuous crystallizer is the fluid overflow therefrom.

13. Apparatus for determining the crystallizati properties of urine to study stone formation therein, comprising:
   a continuous crystallizer chamber for containing fluid which includes synthetic urine and an aliquot of natural urine;
   means for recirculating the fluid from an output of said continuous crystallizer back to an input of the continuous crystallizer; and
   means for measuring the crystal populations of the fluid.

14. Apparatus as defined by claim 13 further comprising means for adding calcium and oxalate ions to said fluid.

15. Apparatus as defined by claim 14 wherein said means for adding calcium and oxalate ions to said fluid includes a calcium oxalate saturator in said recirculating means.

16. Apparatus as defined by claim 15 wherein said means for adding calcium and oxalate ions to said feed further comprises a calcium ion feed and an oxalate ion feed.

17. Apparatus as defined by claim 13 wherein said means for measuring crystal populations comprises means for sampling said fluid and means for measuring the crystal populations of said sample.

18. Apparatus as defined by claim 16 wherein said means for measuring crystal populations comprises means for sampling said fluid and means for measuring the crystal populations of said sample.

19. Apparatus as defined by claim 13 wherein said recirculating means includes at least one filter.

20. Apparatus as defined by claim 18 wherein said recirculating means includes at least one filter.

21. Apparatus as defined by claim 13 wherein said recirculating means includes a pump and a surge tank.

22. Apparatus as defined by claim 20 wherein said recirculating means includes a pump and a surge tank.

23. Apparatus as defined by claim 13 wherein said continuous crystallizer is a mixed suspension mixed product removal crystallizer.

24. Apparatus as defined by claim 18 wherein said continuous crystallizer is a mixed suspension mixed product removal crystallizer.

25. Apparatus for determining the crystallization kinetics of urine to study stone formation therein, comprising:
   a continuous crystallizer chamber for containing a fluid which includes synthetic urine and an aliquot of natural urine;
   means for recirculating the fluid from an output of said continuous crystallizer back to an input of the continuous crystallizer;
   means for sampling the fluid;
   particle counting means for receiving the sampled fluid; and
   computing means responsive to the output of said particle counting means for determining the crystallization kinetics occurring in said crystallizer.

26. Apparatus as defined by claim 25 further comprising means for adding calcium and oxalate ions to said fluid.

27. Apparatus as defined by claim 26 wherein said means for adding calcium and oxalate ions to said fluid includes a calcium oxalate saturator in said recirculating means.

28. Apparatus as defined by claim 27 wherein said means for adding calcium and oxalate ions to said feed further comprises a calcium ion feed and an oxalate ion feed.

29. Apparatus as defined by claim 25 wherein said recirculating means includes at least one filter.

30. Apparatus as defined by claim 28 wherein said recirculating means includes at least one filter.

31. Apparatus as defined by claim 25 wherein said recirculating means includes a pump and a surge tank.

32. Apparatus as defined by claim 30 wherein said recirculating means includes a pump and a surge tank.

* * * * *